US011975309B2

(12) United States Patent
Sabahi et al.

(10) Patent No.: US 11,975,309 B2
(45) Date of Patent: *May 7, 2024

(54) FCC CATALYST WITH ENHANCED MESOPOROSITY, ITS PREPARATION AND USE

(71) Applicant: Ketjen Limited Liability Company, Houston, TX (US)

(72) Inventors: Amir Sabahi, Missouri City, TX (US); Eswaramoorthi Iyyamperumal, Houston, TX (US); Nataly G. Vargas, Pearland, TX (US); William Knowles, Friendswood, TX (US); Andrew Loebl, Charlotte, NC (US); Julie Francis, Houston, TX (US)

(73) Assignee: Ketjen Limited Liability Company, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/960,930

(22) PCT Filed: Jan. 11, 2019

(86) PCT No.: PCT/US2019/013279
§ 371 (c)(1),
(2) Date: Jul. 9, 2020

(87) PCT Pub. No.: WO2019/140249
PCT Pub. Date: Jul. 18, 2019

(65) Prior Publication Data
US 2020/0338536 A1 Oct. 29, 2020

Related U.S. Application Data

(60) Provisional application No. 62/617,176, filed on Jan. 12, 2018.

(51) Int. Cl.
*B01J 29/08* (2006.01)
*B01J 6/00* (2006.01)
(Continued)

(52) U.S. Cl.
CPC ............ *B01J 29/088* (2013.01); *B01J 6/001* (2013.01); *B01J 29/005* (2013.01); *B01J 29/06* (2013.01); *B01J 29/061* (2013.01); *B01J 29/085* (2013.01); *B01J 29/70* (2013.01); *B01J 29/7038* (2013.01); *B01J 29/7049* (2013.01); *B01J 29/7057* (2013.01); *B01J 29/80* (2013.01); *B01J 35/0013* (2013.01); *B01J 35/1033* (2013.01); *B01J 35/1061* (2013.01); *B01J 35/108* (2013.01); *B01J 35/109* (2013.01); *B01J 37/0009* (2013.01); *B01J 37/0045* (2013.01); *B01J 37/036* (2013.01); *B01J 37/038* (2013.01);
(Continued)

(58) Field of Classification Search
CPC ........ B01J 6/001; B01J 29/084; B01J 29/085; B01J 29/088; B01J 29/65; B01J 29/80; B01J 29/40; B01J 29/005; B01J 29/061; B01J 29/06; B01J 29/7007; B01J 29/70; B01J 29/7038; B01J 29/7042; B01J 29/7049; B01J 29/7057; B01J 2029/081; B01J 2029/062; B01J 2229/36; B01J 2229/186; B01J 2229/42; B01J 35/0013; B01J 35/1033; B01J 35/108; B01J 35/109; B01J 37/0009; B01J 37/0045; B01J 37/036; B01J 37/038; B01J 37/10; B01J 37/30; B01J 37/28; C07C 2527/14; C07C 2527/16; C07C 2527/18; C07C 2527/182; C07C 2527/167; C07C 2529/06; C07C 2529/08; C07C 2529/40; C07C 2529/70; C10G 11/05; C10G 11/18; C10G 2300/70
USPC ........ 502/60, 63, 64, 65, 67, 69, 71, 73, 77, 502/79, 84
See application file for complete search history.

(56) References Cited

U.S. PATENT DOCUMENTS 4,086,187 A 4/1978 Lim et al.
6,022,471 A 2/2000 Wachter et al.
(Continued)

FOREIGN PATENT DOCUMENTS

CN 103447070 12/2013
EP 2 027 917 * 2/2009
(Continued)

OTHER PUBLICATIONS

PCT/US2019/013279 International Search Report and Written Opinion of the International Searching Authority, Date of Mailing Apr. 15, 2019.
(Continued)

*Primary Examiner* — Elizabeth D Wood

(57) ABSTRACT

Process for the preparation of a catalyst and a catalyst comprising enhanced mesoporosity is provided herein. Thus, in one embodiment, provided is a particulate FCC catalyst comprising 2 to 50 wt % of one or more ultra stabilized high SiO2/Al2O3 ratio large pore faujasite zeolite or a rare earth containing USY, 0 to 50 wt % of one or more rare-earth exchanged large pore faujasite zeolite, 0 to 30 wt % of small to medium pore size zeolites, 5 to 45 wt % quasi-crystalline boehmite 0 to 35 wt % microcrystalline boehmite, 0 to 25 wt % of a first silica, 2 to 30 wt % of a second silica, 0.1 to 10 wt % one or more rare earth components showiomg enhanced mesoporosity in the range of 6-40 nm, the numbering of the silica corresponding to their orders of introduction in the preparation process.

10 Claims, 3 Drawing Sheets

(51) Int. Cl.
*B01J 29/00* (2006.01)
*B01J 29/06* (2006.01)
*B01J 29/70* (2006.01)
*B01J 29/80* (2006.01)
*B01J 35/00* (2006.01)
*B01J 35/10* (2006.01)
*B01J 37/00* (2006.01)
*B01J 37/03* (2006.01)
*B01J 37/06* (2006.01)
*B01J 37/10* (2006.01)
*B01J 37/28* (2006.01)
*B01J 37/30* (2006.01)
*C10G 11/05* (2006.01)
*C10G 11/18* (2006.01)
*B01J 29/40* (2006.01)
*B01J 29/65* (2006.01)

(52) U.S. Cl.
CPC ............... *B01J 37/06* (2013.01); *B01J 37/10* (2013.01); *B01J 37/28* (2013.01); *B01J 37/30* (2013.01); *C10G 11/05* (2013.01); *C10G 11/18* (2013.01); *B01J 2029/062* (2013.01); *B01J 29/40* (2013.01); *B01J 29/65* (2013.01); *B01J 29/7007* (2013.01); *B01J 29/7042* (2013.01); *B01J 2229/186* (2013.01); *B01J 2229/36* (2013.01); *B01J 2229/42* (2013.01); *C07C 2527/14* (2013.01); *C07C 2527/16* (2013.01); *C07C 2527/167* (2013.01); *C07C 2527/18* (2013.01); *C07C 2527/182* (2013.01); *C07C 2529/06* (2013.01); *C07C 2529/08* (2013.01); *C07C 2529/40* (2013.01); *C07C 2529/70* (2013.01)

(56) References Cited

U.S. PATENT DOCUMENTS

| | | | |
|---|---|---|---|
| 6,903,040 B2 * | 6/2005 | Stamires | C01F 7/02 502/60 |
| 6,930,067 B2 | 8/2005 | O'Connor et al. | |
| 7,459,413 B2 | 12/2008 | Shen et al. | |
| 7,504,021 B2 | 3/2009 | Wachter et al. | |
| 9,486,795 B2 | 11/2016 | Long et al. | |
| 9,534,177 B2 | 1/2017 | Babitz | |
| 9,643,166 B2 | 5/2017 | Stamires et al. | |
| 9,656,255 B2 | 5/2017 | Long et al. | |
| 9,844,772 B2 | 12/2017 | Gao et al. | |
| 10,807,076 B2 | 10/2020 | Sigman et al. | |
| 2003/0003035 A1 | 1/2003 | Stamires et al. | |
| 2003/0166453 A1 | 9/2003 | Kuvettu et al. | |
| 2005/0250642 A1 * | 11/2005 | Stamires | C01F 7/448 502/64 |
| 2010/0152024 A1 * | 6/2010 | Stamires | B01J 37/0045 502/62 |
| 2013/0203586 A1 * | 8/2013 | Stamires | C10G 29/205 502/68 |
| 2014/0116923 A1 | 5/2014 | Dinda et al. | |
| 2015/0375218 A1 | 12/2015 | Koseoglu et al. | |

FOREIGN PATENT DOCUMENTS

| | | |
|---|---|---|
| EP | 1863588 B1 | 11/2017 |
| JP | 2004-130169 | 4/2004 |
| WO | 2002/098563 | 12/2002 |
| WO | 2005123252 | 12/2005 |
| WO | 2006/067154 | 6/2006 |
| WO | WO 2006/067154 * | 6/2006 |
| WO | 2007/006047 | 1/2007 |
| WO | 2013005225 | 1/2013 |
| WO | 2015/057841 A1 | 4/2015 |
| WO | 2015179735 | 11/2015 |
| WO | 2018/027173 A1 | 2/2018 |

OTHER PUBLICATIONS

PCT/US2019/013279 International Preliminary Report of Patentability Authority, Date of Mailing Jul. 14, 2020.
V.P.Doronin et al., Advanced Developments: Cracking Catalysts and Additivies thereto, issu 5, 2014, p. 82-87.
D.B. Tagiev, Kh.M.Minachev "Catalytic Properties of Zeolites in the Oxidation Reaction", Success of Chemistry, Nov. 1981, vol. L, issue 11, annotation, pp. 1929-1959.
I.P.Mukhlenov, Catalyst Technology 3d edition, Leningrad Branch, 1989, 272 pages. see p. 95, paragraph 1.

* cited by examiner

| | Base Catalyst #1 | New Catalyst #1 | New Catalyst #2 | Base Catalyst #2 | New Catalyst #3 | New Catalyst #4 |
|---|---|---|---|---|---|---|
| Total Pore Volume Between ~2.0 To ~80 nm(cc/g) | 0.1676 | 0.2367 | 0.2363 | 0.1569 | 0.2398 | 0.2336 |
| Pore Volume Between ~2.0 To 6 nm(cc/g) | 0.07316 | 0.06477 | 0.06699 | 0.06108 | 0.06634 | 0.05939 |
| % Pore Volume Between Pore Diameter ~2.0 To 6 nm | 44% | 27% | 28% | 39% | 28% | 25% |
| Pore Volume Between 6-40 nm (cc/g) | 0.08254 | 0.15953 | 0.15461 | 0.08252 | 0.16136 | 0.15881 |
| % Pore Volume Between Pore Diameter 6 To 40 nm | 49% | 67% | 65% | 53% | 67% | 68% |

|  | Base Catalyst -3 | New Catalyst -5 | New Catalyst -6 |
|---|---|---|---|
| Total Pore Volume Between ~2 To ~80 nm(cc/g) | 0.2045 | 0.2319 | 0.2312 |
| Pore Volume Between ~2 To 6 nm(cc/g) | 0.07863 | 0.05258 | 0.05302 |
| % Pore Volume Between Pore Diameter 2 To 6 nm | 38% | 23% | 23% |
| Pore Volume Between 6-40 nm (cc/g) | 0.09817 | 0.16042 | 0.15898 |
| % Pore Volume Between Pore Diameter 6 To 40 nm | 48% | 69% | 69% |

|  | Base Catalyst #4 | New Catalyst #7 | New Catalyst #8 | Base Catalyst #9 | New Catalyst #10 | New Catalyst #11 |
|---|---|---|---|---|---|---|
| Total Pore Volume Between ~2.0 To ~80 nm(cc/g) | 0.2029 | 0.2432 | 0.2259 | 0.2260 | 0.2021 | 0.2026 |
| Pore Volume Between ~2.0 To 6 nm(cc/g) | 0.08945 | 0.07053 | 0.06749 | 0.06358 | 0.06375 | 0.06163 |
| % Pore Volume Between Pore Diameter ~2.0 To 6 nm | 44% | 29% | 30% | 28% | 32% | 30% |
| Pore Volume Between 6-40 nm (cc/g) | 0.08085 | 0.14827 | 0.13551 | 0.13842 | 0.11085 | 0.11577 |
| % Pore Volume Between Pore Diameter 6 To 40 nm | 40% | 61% | 60% | 61% | 55% | 57% |

FCC CATALYST WITH ENHANCED MESOPOROSITY, ITS PREPARATION AND USE

FIELD OF THE INVENTION

The present invention pertains to a catalyst composition and its use in a process for the cracking or conversion of a feed comprised of hydrocarbons, such as, for example, those obtained from the processing of crude petroleum, with better physical properties and performance.

BACKGROUND

A common challenge in the design and production of heterogeneous catalysts is to find a good compromise between the effectiveness and/or accessibility of the active sites and the effectiveness of the immobilising matrix in giving the catalyst particles sufficient physical strength, i.e. attrition resistance. Further, there is a need to develop a catalyst or catalytic system with better coke selectivity.

The preparation of attrition resistant catalysts is disclosed in several prior art documents. U.S. Pat. No. 4,086,187 discloses a process for the preparation of an attrition resistant catalyst by spray-drying an aqueous slurry prepared by mixing (i) a faujasite zeolite with a sodium content of less than 5 wt % with (ii) kaolin, (iii) peptised pseudoboehmite, and (iv) ammonium polysilicate. The attrition resistant catalysts according to U.S. Pat. No. 4,206,085 are prepared by spray-drying a slurry prepared by mixing two types of acidified pseudoboehmite, zeolite, alumina, clay, and either ammonium polysilicate or silica sol.

WO 02/098563 discloses a process for the preparation of an FCC catalyst having both a high attrition resistance and a high accessibility. The catalyst is prepared by slurrying zeolite, clay, and boehmite, feeding the slurry to a shaping apparatus, and shaping the mixture to form particles, characterised in that just before the shaping step the mixture is destabilised. This destabilisation is achieved by, e.g., temperature increase, pH increase, pH decrease, or addition of gel-inducing agents such as salts, phosphates, sulphates, and (partially) gelled silica. Before destabilisation, any peptisable compounds present in the slurry must have been well peptised.

WO 06/067154 describes an FCC catalyst, its preparation and its use. It discloses a process for the preparation of an FCC catalyst having both a high attrition resistance and a high accessibility. The catalyst is prepared by slurrying a clay, zeolite, a sodium-free silica source, quasi-crystalline boehmite, and micro-crystalline boehmite, provided that the slurry does not comprise peptised quasi-crystalline boehmite, b) adding a monovalent acid to the slurry, c) adjusting the pH of the slurry to a value above 3, and d) shaping the slurry to form particles.

WO2015057841 discloses a mesoporous catalyst formed by combining a matrix precursor treated with a polyphosphate, and a metallic oxide treated with a cationic electrolyte. The combined treatment with the polyphosphate and cationic polyelectrolyte yields unexpected improvements in attrition resistance, while maintaining high overall pore volume, even as the ratio of mesopore volume to macropore volume of the formed FCC catalyst increases.

U.S. Pat. No. 6,022,471 discloses an FCC catalyst having improved coke selectivity and an FCC process for converting hydrocarbon feedstocks to lower boiling products. The catalyst comprises a crystalline aluminosilicate zeolite, gibbsite, rare earth metal compound and a silica matrix prepared from at least one of a silica sol made by an ion-exchange process and an acidic silica sol prepared by mixing sodium silicate, an acid and an aluminum salt of an acid. The matrix material is mesoporous having pore diameters in the range between about 100 to 300 Å and may contain two different types of silica sols, and preferably a clay component. A first type of silica sol is made by an ion-exchange process. The second type of silica sol is prepared by reacting sodium silicate with a mineral acid followed by addition of an aluminum salt.

BRIEF DESCRIPTION OF THE INVENTION

Figure 1:
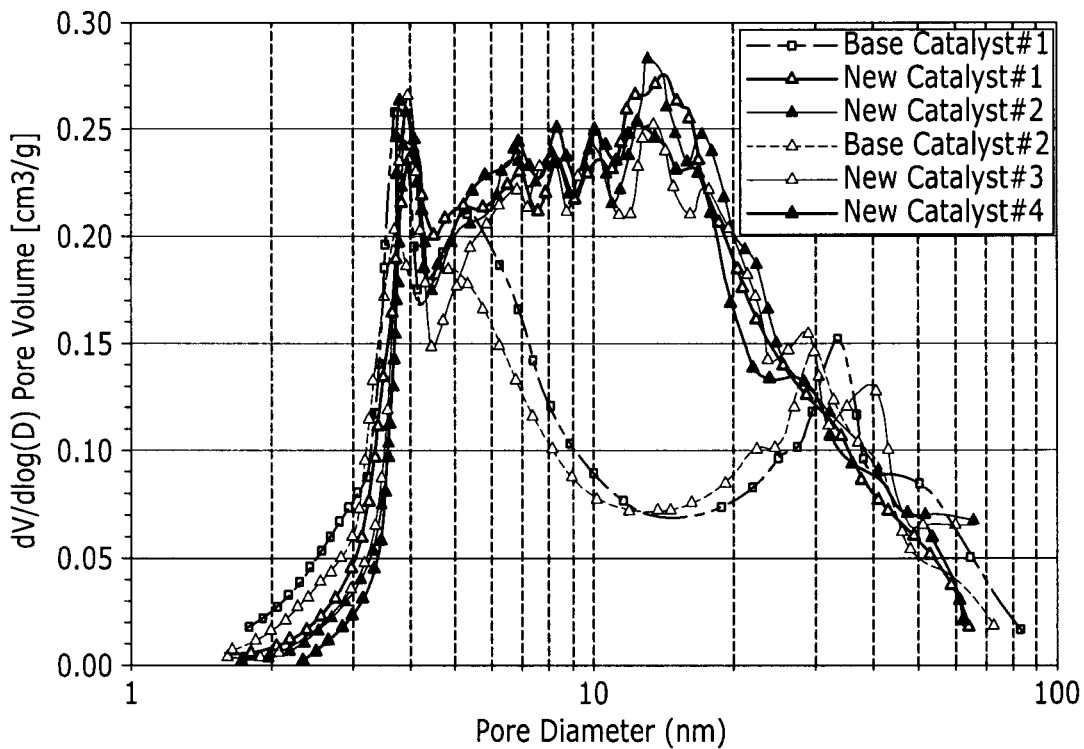
FIG. 1 is a graph showing the pore volume distribution based on pore diameter for the base catalyst and new catalyst formulations in Example 1.
Figure 2:
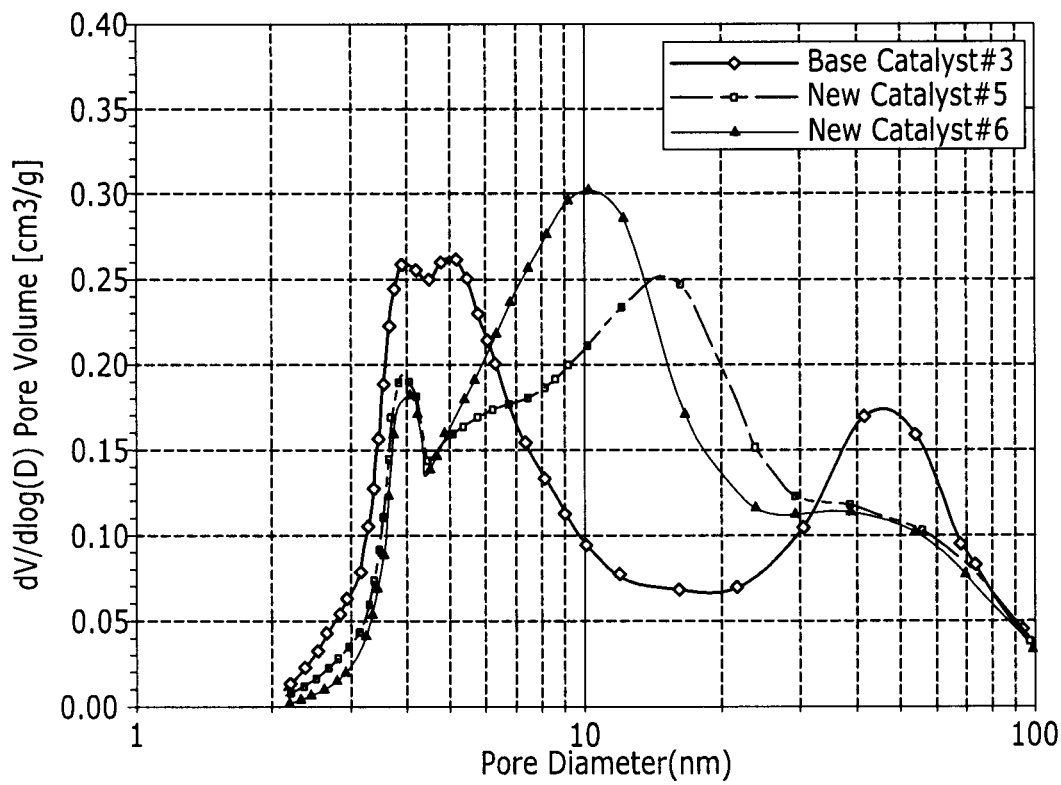
FIG. 2 is a graph showing the pore volume distribution based on pore diameter for the base catalyst and new catalyst formulations in Example 4.
Figure 3:
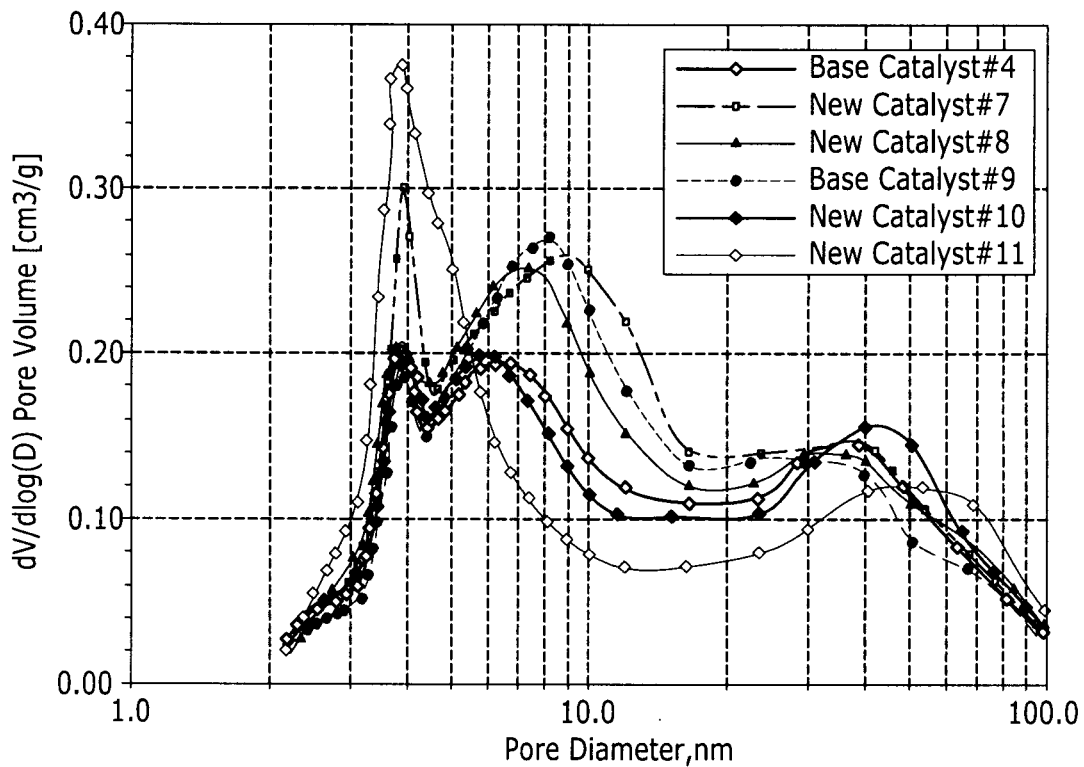
FIG. 3 is a graph showing the pore volume distribution based on pore diameter for the base catalysts and new catalyst formulations in Example 5.

The present invention relates to an FCC catalyst meant to be employed in the process for cracking, a hydrocarbon feed over a particular catalyst composition to produce conversion product hydrocarbon compounds of lower molecular weight than feed hydrocarbons, e.g., product comprising a high gasoline fraction.

Thus, in one embodiment, provided is a particulate FCC catalyst comprising about 2 to about 50 wt % of one or more ultra stabilized high $SiO_2/Al_2O_3$ ratio large pore faujasite zeolite (framework $SiO_2/Al_2O_3$ ratio above ~6.5) or a rare earth containing USY (framework $SiO_2/Al_2O_3$ ratio above ~6.5), 0 to about 50 wt % of one or more rare-earth exchanged large pore faujasite zeolite, 0 to about 30 wt % of small to medium pore size zeolites, about 5 to about 45 wt % quasi-crystalline boehmite (QCBs) about 0 to about 35 wt % microcrystalline boehmite (MCBs), 0 to about 25 wt % of a first silica, about 2 to about 30 wt % of a second silica from acidic colloidal silica or ammonia stabilized colloidal silica or low-sodium stabilized colloidal silica or polysilicic acid, about 0.1 to about 10 wt % one or more rare earth components and the balance clay, shows enhanced mesoporosity in the range of 6-40 nm after industrially recognized deactivation.

In another embodiment, provided is a process for manufacturing an FCC catalyst, wherein the process comprises:
 (a) Adding, clay, one or more boehmites and sodium stabilized colloidal silica to form a slurry;
 (b) Digesting the slurry with a monoprotic acid to a pH of less than 4;
 (c) Adding a rare earth exchanged zeolite to the slurry;
 (d) Making a mixture of ultra stabilized zeolite, acidic colloidal silica and a rare earth component;
 (e) Adding this second slurry to the first slurry;
 (f) Mixing the slurry and then destabilizing the slurry by raising the pH to above 4.0;
 (g) Shaping and collecting the resulting FCC Catalyst;
 (h) Optionally followed by a calcination step and post washing step to remove excess sodium as necessary.

In another embodiment, provided is a process for manufacturing an FCC catalyst, wherein the process comprises:
 (a) Adding, clay, boehmite, sodium stabilized colloidal silica to form a slurry;

(b) Digesting the slurry with a monoprotic acid to a pH of less than 4;
(c) Adding one or more zeolites to the slurry;
(d) Adding a rare earth component to the slurry either after step (a) or after step (b) and mixing;
(e) Adding low or sodium free poly silicic acid in line or addition of acidic colloidal silica or ammonia stabilized or low-sodium stabilized colloidal anywhere in the above steps a-e;
(f) Destabilizing the slurry by raising the pH to above 4.0;
(g) Shaping and collecting the resulting FCC Catalyst;
(h) Optionally followed by a calcination and post washing step to remove excess sodium as necessary.

In another embodiment, provided is a process for manufacturing an FCC catalyst, wherein the process comprises:
(a) Adding, clay, boehmite, colloidal silica to form a slurry;
(b) Digesting the slurry with a monoprotic acid to a pH of less than 4;
(c) Adding one or more zeolites from the group of ultra stabilized Y zeolite, rare earth exchanged ultra stabilized high SiO2/Al2O3 Y zeolite, rare earth exchanged Y zeolites, zeolites with Pentasil and beta structures to the slurry;
(d) Optionally adding rare earth oxide component to the slurry and mixing;
(e) Adjust the slurry pH to below 4 with monoprotic acid;
(f) Adding low or sodium free poly silicic acid in line or addition of acidic colloidal silica or ammonia stabilized or low-sodium stabilized colloidal anywhere in the above steps a-e.
(g) Destabilizing the slurry by raising the pH to above 4.0;
(h) Shaping and collecting the resulting FCC catalyst;
(i) Optionally followed by a calcination and post washing step to remove excess sodium as necessary.

In yet a further embodiment, provided is a process for manufacturing an FCC catalyst, wherein the process comprises:
(a) Adding, clay, boehmite, sodium stabilized colloidal silica to form a slurry;
(b) Digesting the slurry with a monoprotic acid to a pH of less than 4;
(c) Adding one or more zeolites from the group of ultra stabilized high SiO2/Al2O3 Y zeolite, rare earth exchanged USY, rare earth exchanged Y zeolites, zeolites with Pentasil and beta structures to the slurry;
(d) Adding a rare earth component to the slurry either after step (a) or after step (c) and mixing;
(e) Adjust the slurry pH to below 4 with monoprotic acid;
(f) Adding low or sodium free poly silicic acid in line or addition of acidic colloidal silica or ammonia stabilized or low-sodium stabilized colloidal anywhere in the above steps a-e;
(g) Destabilizing the slurry by raising the pH to above 4.0;
(h) Shaping and collecting the resulting FCC Catalyst;
(i) Optionally followed by a calcination and post washing step to remove excess sodium as necessary.

The resulting catalyst shows improved benefits over that known in the art. For example, the improved catalyst exhibits improved attrition and higher ABD and accessibility. Further, the improved catalyst results in better coke selectivity at constant conversion with more bottoms upgrading.

In a still further embodiment, provided is a process for cracking a petroleum fraction feedstock said process comprising the steps of:
a) providing an FCC catalyst composition comprising about 2 to about 50 wt % of one or more ultra stabilized high SiO2/Al2O3 ratio large pore faujasite zeolite or a rare earth containing USY, 0 to about 50 wt % of one or more rare-earth exchanged large pore faujasite zeolite, 0 to 30 wt % of small-medium pore size zeolites (Pentasil, beta, etc), about 5 to about 45 wt % quasicrystalline boehmite, about 0 to about 35 wt % microcrystalline boehmite, about 0 to about 20 wt % silica from sodium stabilized colloidal silica, about 2 to about 30 wt % silica from acidic colloidal silica or ammonia stabilized colloidal silica or low-sodium stabilized colloidal silica or polysilicic acid, about 0.1 to about 10 wt % of rare earth component as oxide, and the balance clay;
b) contacting the FCC catalyst with said petroleum fraction feedstock at a temperature in the range of from 400 to 650° C., with a dwell time in the range of from 0.5 to 12 seconds.

These and still other embodiments, advantages and features of the present invention shall become further apparent from the following detailed description, including the appended claims.

DETAILED DESCRIPTION OF THE INVENTION

Unless otherwise indicated, weight percent (_____ wt %) as used herein is the dry base weight percent of the specified form of the substance, based upon the total dry base weight of the product for which the specified substance or form of substance is a constituent or component. It should further be understood that, when describing steps or components or elements as being preferred in some manner herein, they are preferred as of the initial date of this disclosure, and that such preference(s) could of course vary depending upon a given circumstance or future development in the art.

General Procedure

The first step of the process of manufacturing the improved catalyst is to mix clay sources with colloidal silica, and one or more alumina (boehmite) sources. As will be discussed below, one can optionally add a second silica source of acidic colloidal silica or ammonia stabilized or low-sodium stabilized colloidal to this slurry or at a later step. The clay, zeolite, QCB, MCB, colloidal silica, and optional other components can be slurried by adding them to water as dry solids. Alternatively, slurries containing the individual materials are mixed to form the slurry. It is also possible to add some of the materials as slurries, and others as dry solids. Optionally, other components may be added, such as aluminium chlorohydrol, aluminium nitrate, $Al_2O_3$, $Al(OH)_3$, anionic clays (e.g. hydrotalcite), smectites, sepiolite, barium titanate, calcium titanate, calcium-silicates, magnesium-silicates, magnesium titanate, mixed metal oxides, layered hydroxy salts, additional zeolites, magnesium oxide, bases or salts, and/or metal additives such as compounds containing an alkaline earth metal (for instance Mg, Ca, and Ba), a Group IIIA transition metal, a Group IVA transition metal (e.g. Ti, Zr), a Group VA transition metal (e.g. V, Nb), a Group VIA transition metal (e.g. Cr, Mo, W), a Group VIIA transition metal (e.g. Mn), a Group VIIIA transition metal (e.g. Fe, Co, Ni, Ru, Rh, Pd, Pt), a Group IB transition metal (e.g. Cu), a Group IIB transition metal (e.g. Zn), a lanthanide (e.g. La, Ce), or mixtures thereof. Any order of addition of these compounds may be used. It is also possible to combine these compounds all at the same time.

The term "boehmite" is used in the industry to describe alumina hydrates which exhibit X-ray diffraction (XRD) patterns close to that of aluminium oxide-hydroxide [AlO (OH)]. Further, the term boehmite is generally used to describe a wide range of alumina hydrates which contain different amounts of water of hydration, have different surface areas, pore volumes, specific densities, and exhibit different thermal characteristics upon thermal treatment. Yet their XRD patterns, although they exhibit the characteristic boehmite [AlO(OH)] peaks, usually vary in their widths and can also shift in their location. The sharpness of the XRD peaks and their location has been used to indicate the degree of crystallinity, crystal size, and amount of imperfections.

Broadly, there are two categories of boehmite aluminas: quasi-crystalline boehmites (QCBs) and micro-crystalline boehmites (MCBs). In the state of the art, quasi-crystalline boehmites are also referred to as pseudo-boehmites and gelatinous boehmites. Usually, these QCBs have higher surface areas, larger pores and pore volumes, and lower specific densities than MCBs. They disperse easily in water or acids, have smaller crystal sizes than MCBs, and contain a larger number of water molecules of hydration. The extent of hydration of QCB can have a wide range of values, for example from about 1.4 up to about 2 moles of water per mole of Al, intercalated usually orderly or otherwise between the octahedral layers. Some typical commercially available QCBs are Pural®, Catapal®, and Versal® products.

Microcrystalline boehmites are distinguished from the QCBs by their high degree of crystallinity, relatively large crystal size, very low surface areas, and high densities. Contrary to QCBs, MCBs show XRD patterns with higher peak intensities and very narrow half-widths. This is due to their relatively small number of intercalated water molecules, large crystal sizes, the higher degree of crystallization of the bulk material, and the smaller amount of crystal imperfections. Typically, the number of water molecules intercalated can vary in the range from about 1 up to about 1.4 per mole of Al.

The first source of silica is typically a low sodium silica source and is generally added to the initial slurry. Examples of such silica sources include, but are not limited to potassium silicate, sodium silicate, lithium silicate, calcium silicate, magnesium silicate, barium silicate, strontium silicate, zinc silicate, phosphorus silicate, and barium silicate. Examples of suitable organic silicates are silicones (polyorganosiloxanes such as polymethylphenylsiloxane and polydimethylsiloxane) and other compounds containing Si—O—C—O—Si structures, and precursors thereof such as methyl chlorosilane, dimethyl chlorosilane, trimethyl chlorosilane, and mixtures thereof. Preferred low sodium silica sources are sodium stabilized colloidal silicas. The slurry further comprises about 0 to about 25 wt % and more preferably about 0 to about 20 wt % of silica from the sodium-free silicon source based on the weight of the final catalyst.

The second silica source is typically an acidic or low sodium or sodium free colloidal silica or polysilicic acid or ammonia stabilized or other low-sodium stabilized colloidal silica. Suitable silicon sources to be added as a second silica source include (poly)silicic acid, sodium silicate, sodium-free silicon sources, and organic silicon sources. One such source for the second silica is a sodium stabilized or sodium free polysilicic acid made inline of the process by mixing appropriate amounts of sulfuric acid and water glass. The acidic colloidal silica is acid stabilized sodium-free or low sodium amorphous colloidal silica particles dispersed in water or any suitable solvent. Ammonia (pH=8-10.5, PSD=5-85 nm) or low-sodium stabilized colloidal silica (pH=5-8, PSD=5-85 nm) can also be used in place of acidic colloidal silica. This second addition of silica is generally added in an amount of about 5 to 25 wt %, and preferably about 5 to about 20% based on the weight of the final catalyst.

The choice of the second silica source can have an effect on when the material is added to the slurry discussed above. If acidic colloidal silica is used, then the silica may be added at any step prior to the pH adjustment step. However, if the second silica source is a sodium stabilized or sodium free polysilicic acid or ammonia stabilized or low-sodium stabilized colloidal, the silica should be added after the zeolite addition just prior to the pH adjustment step. In addition, due to the sodium content of the polysilicic acid it may be necessary to wash the final catalyst to remove excess sodium. It may further be necessary to calcine the final catalyst.

The clay is preferred to have a low sodium content (less than 0.1 wt % $Na_2O$), or to be sodium-free. Suitable clays include kaolin, bentonite, saponite, sepiolite, attapulgite, laponite, hectorite, English clay, anionic clays such as hydrotalcite, and heat- or chemically treated clays such as meta-kaolin. The slurry preferably comprises about 0 to about 70 wt %, more preferably about 10 to about 60 wt %, and most preferably about 10 to about 50 wt % of clay.

In a next step, a monovalent acid is added to the suspension, causing digestion. Both organic and inorganic monovalent acids can be used, or a mixture thereof. Examples of suitable monovalent acids are formic acid, acetic acid, propionic acid, nitric acid, and hydrochloric acid. The acid is added to the slurry in an amount sufficient to obtain a pH lower than 7, more preferably between 1 and 4.

One or more zeolites can then be added. The zeolites used in the process according to the present invention preferably have a low sodium content (less than 1.5 wt % $Na_2O$), or are sodium-free. Suitable zeolites to be added include typical zeolites for the application such as Y-zeolites including HY, USY, dealuminated Y, RE-Y, and RE-USY zeolite beta, ZSM-5, phosphorus-activated ZSM-5, ion-exchanged ZSM-5, MCM-22, and MCM-36, metal-exchanged zeolites, ITQs, SAPOs, ALPOs, and mixtures thereof. In particular, one or more ultra stabilized high SiO2/Al2O3 ratio large pore faujasite zeolite (framework SiO2/Al2O3 ratio above about 6.5) or a rare earth containing USY (framework SiO2/Al2O3 ratio above about 6.5) are utilized. In particular, about 2 to about 50 wt % of one or more ultra stabilized high Y zeolite or RE-USY is utilized in the catalyst. In addition, about 0 to about 50 wt % of one or more rare-earth exchanged Y zeolite can be added to the one or more ultra stabilized high Y zeolite or RE-USY.

Optionally, small to medium pore size zeolites can be added to the mixture at this time. Typically, the amount is added in an amount of about 0 to about 30 wt %. Any suitable medium pore zeolite may be used. Such suitable medium pore zeolites include but are not limited to ZSM-5, ZSM-11, ZSM-22, Beta, or Ferrierite A rare earth component is added in an amount of about 0.1 to about 10 wt %, based on the oxide form, in the form of a salt or solution to the mixture. Examples of suitable rare earth elements include but not limited to lanthanum, yttrium and cerium. The rare earth is typically added as hydroxide, chloride, oxide, nitrate, sulfate, oxychlorides, acetates, or carbonates. Preferably, lanthanum nitrate is added in an amount of about 0.1 to about 10 wt % based on the oxide form in the form of a salt or solution. The rare earth component can be added before or after the peptization (or digestion) of the alumina as described above.

The above combined slurry is then passed through a high sheer mixer where it is destabilized by increasing the pH. The pH of the slurry is subsequently adjusted to a value above 3, more preferably above 3.5, even more preferably above 4. The pH of the slurry is preferably not higher than 7, because slurries with a higher pH can be difficult to handle. The pH can be adjusted by adding a base (e.g. NaOH or NH$_4$OH) to the slurry. The time period between the pH adjustment and shaping step preferably is 30 minutes or less, more preferably less than 5 minutes, and most preferably less than 3 minutes. At this step, the solids content of the slurry preferably is about 10 to about 45 wt %, more preferably about 15 to about 40 wt %, and most preferably about 25 to about 35 wt %.

The slurry is then shaped. Suitable shaping methods include spray-drying, pulse drying, pelletising, extrusion (optionally combined with kneading), beading, or any other conventional shaping method used in the catalyst and absorbent fields or combinations thereof. A preferred shaping method is spray-drying. If the catalyst is shaped by spray-drying, the inlet temperature of the spray-dryer preferably ranges from 300 to 600° C. and the outlet temperature preferably ranges from 105 to 200° C.

The Resulting Catalyst

The catalyst so obtained has exceptionally good attrition resistance and accessibility. Therefore, the invention also relates to a catalyst obtainable by the process according to the invention. The catalyst is generally an FCC catalyst comprising about 2 to about 50 wt % of one or more ultra stabilized high SiO2/Al2O3 ratio Y zeolite or RE-USY, 0 to about 50 wt % of one or more rare-earth exchanged Y zeolite, 0 to about 30 wt % of small to medium pore size zeolites, about 5 to about 35 wt % quasicrystalline boehmite, about 0 to about 50 wt % microcrystalline boehmite, about 0 to about 20 wt % silica from sodium stabilized colloidal silica, about 2 to about 30 wt % silica from acidic colloidal silica or polysilicic acid or ammonia stabilized colloidal silica or low-sodium colloidal silica, about 0.1 to about 10 wt % rare earth component as measured by its oxide and the balance clay.

A key feature of the resulting catalyst is an increase in mesoporosity over previous catalysts. The BJH pore size distribution from N2 physisorption measurements for catalysts of the present invention along with standard base catalysts after industrially recognized cyclic deactivation in presence of Ni/V and steam are shown in the figures. It indicates that the catalysts of the present invention have increased mesopores in the range of 6-40 nm compared to standard base catalysts. It is clear from the table given that the pore diameter distribution having a peak at a pore diameter of about 2.0 to 6 nm has around 20-30% of total pore volume and the pore volume of pores with diameter 6 to 40 nm is around 55-70% of total pore volume, more preferably 60-70%. Whereas the base catalysts showed almost equal contribution of pore volume from the pores with above mentioned pore diameter ranges. The results indicate that the catalysts of the present invention moved significant amount of pores with diameter about 2.0 to 6 nm to mesopores of 6 to 40 nm. It is believed, an increase in mesoporosity improves the performance of the catalysts of the present invention in FCC testing with resid feed. It is believed, the increased mesopores may favor more selective cracking, particularly with larger molecules that leads to less coke and more bottoms upgrading.

These catalysts can be used as FCC catalysts or FCC additives in hydroprocessing catalysts, alkylation catalysts, reforming catalysts, gas-to-liquid conversion catalysts, coal conversion catalysts, hydrogen manufacturing catalysts, and automotive catalysts. The process of the invention is particularly applicable to Fluid Catalytic Cracking (FCC). In the FCC process, the details of which are generally known, the catalyst, which is generally present as a fine particulate comprising over 90 wt % of the particles having diameters in the range of about 5 to about 300 microns. In the reactor portion, a hydrocarbon feedstock is gasified and directed upward through a reaction zone, such that the particulate catalyst is entrained and fluidized in the hydrocarbon feedstock stream. The hot catalyst, which is coming from the regenerator, reacts with the hydrocarbon feed which is vaporized and cracked by the catalyst. Typically temperatures in the reactor are 400-650 C and the pressure can be under reduced, atmospheric or superatmospheric pressure, usually about atmospheric to about 5 atmospheres. The catalytic process can be either fixed bed, moving bed, or fluidized bed, and the hydrocarbon flow may be either concurrent or countercurrent to the catalyst flow. The process of the invention is also suitable for TCC (Thermofor catalytic cracking) or DCC.

EXAMPLES

Prior to any lab testing the catalyst must be deactivated to simulate catalyst in a refinery unit, this is typically done with steam. These samples were deactivated either by cyclic deactivation with Ni/V which consists of cracking, stripping and regeneration steps in the presence of steam or with 100% steam at higher temperatures, which are industrially accepted deactivation methods for FCC catalysts. The deactivation step is known in the art, and is necessary to catalytic activity. In commercial FCC setting, deactivation occurs shortly after catalyst introduction, and does not need to be carried out as a separate step. The Fluid microactivity test, or Fluidized-bed Simulation Test (FST) or Advanced Cracking Evaluation (ACE) is a test known and generally accepted in the art for ascertaining the FCC cracking activity of a catalyst. In ACE the test is conducted with a series of four catalyst-to-feed ratios (CTO) which are obtained by varying the mass of feed injected to the reactor, while using the same amount of catalyst for all runs. The testing apparatus simulates the cracking of a known amount of a hydrocarbon feedstock of known amount and compositional characteristics. This small scale testing unit is a once through unit and operated approximately as in ASTM 5154-10.

The accessibility of the catalysts prepared according to the Examples below was measured by adding 1 g of the catalyst to a stirred vessel containing 50 ml vacuum gas oil diluted in toluene. The solution was circulated between the vessel and a spectrophotometer, in which process the VGO-concentration was continuously measured.

The attrition resistance of the catalysts was measured using a method substantially based on ASTM 5757 Standard Test Method for Determination of Attrition and Abrasion of Powdered Catalysts by Air Jets, the results from which indicate that the more attrition resistant the catalyst is, the lower the resulting attrition index value observed when testing a material using the above-referenced method.

The pore size distribution of deactivated catalysts was measured by BJH method from nitrogen adsorption isotherms following ASTM D4641 method.

Example 1: Four catalysts were made using the above methodologies. The base cases are commercial catalysts. The total zeolite in base case is 21 wt %, whereas in catalysts of the present invention are 25 wt %. The components of the various samples made is shown below:

| Catalyst Description | Base catalyst#1 | New Catalyst#1 | New Catalyst#2 | Base catalyst#2 | New Catalyst#3 | New Catalyst#4 |
|---|---|---|---|---|---|---|
| RE-Y Zeolite | 21.0 | 9.0 | 9.0 | 21.0 | 9.0 | 9.0 |
| USY | 0.0 | 16.0 | 16.0 | 0.0 | 16.0 | 16.0 |
| Quasi-crystalline boehmite | 20.0 | 20.0 | 20.0 | 20.0 | 20.0 | 20.0 |
| Micro-crystalline boehmite | 15.0 | 25.0 | 25.0 | 15.0 | 25.0 | 25.0 |
| Low sodium colloidal silica | 1.5 | 5.0 | 5.0 | 1.5 | 5.0 | 5.0 |
| Acidic colloidal silica | 0.0 | 15.0 | 15.0 | 0.0 | 15.0 | 15.0 |
| RE component | 0.0 | 4.0 | 4.0 | 0.0 | 4.0 | 4.0 |
| Clay | 42.5 | 6.0 | 6.0 | 42.5 | 6.0 | 6.0 |

| Catalyst Description | Base catalyst#1 | New Catalyst#1 | New Catalyst#2 | Base catalyst#2 | New Catalyst#3 | New Catalyst#4 |
|---|---|---|---|---|---|---|
| ABD | 0.72 | 0.72 | 0.73 | 0.73 | 0.74 | 0.74 |
| Attrition | 1.81 | 2.00 | 1.63 | 1.93 | 1.28 | 1.37 |
| Accessibility | 11.6 | 16.2 | 16.5 | 12.3 | 16.1 | 16.1 |
| Sample PV | 0.43 | 0.47 | 0.48 | 0.42 | 0.41 | 0.42 |
| SA BET | 223 | 297 | 293 | 218 | 296 | 295 |
| MSA | 107 | 151 | 150 | 105 | 149 | 148 |
| MIPV | 0.0540 | 0.0678 | 0.0662 | 0.0524 | 0.0682 | 0.0683 |

Based on the results of Example 1, the catalysts of the present invention showed higher surface areas, higher accessibility and at least comparable if not improved attrition.

Example 2 Pore size distribution: Each of the samples from Example 1 was tested for pore size distribution. The deactivated catalysts showed enhanced mesoporosity in the range of 6 to 40 nm compared to base catalysts as shown in the figure below. The pore diameter distribution having a peak at a pore diameter of about 2 to 6 nm has around 25-28% of total pore volume and the pore volume of pores with diameter 6 to 40 nm is around 65-68% of total pore volume for the catalysts of the present invention. In the base catalyst, the pore volume contribution of pores with diameter around 2 to 6 nm is around 39% and 44%, and that of pores with diameter 6 to 40 nm is 49% and 53%. This indicates that the catalysts of the present invention showed enhanced mesopores in the range of 6 to 40 nm, which resulted in improved coke selectivity and bottoms upgrading as shown in the ACE testing results in the table below.

Example 3: The ACE performance evaluation of these catalysts along with base catalysts in resid feed is given below. The catalysts of the present invention were found to be highly active compared to base control catalysts. The coke selectivities of catalysts at constant conversion are better (lower coke) with higher bottoms upgrading than base catalysts. The better performance of the catalysts coke selectivity and bottoms upgrading can be related to the increased mesoporosity on these catalysts compared to base catalysts.

Example 4: In the second example given below, where catalysts of the present invention were prepared by the methods described above. As seen before, better binding and accessibility are noted on the present catalysts of the invention compared to the base catalyst.

| Catalyst Description | Base Catalyst#3 | New catalyst#5 | New catalyst#6 |
|---|---|---|---|
| RE-Y zeolite | 23.00 | 11.0 | 11.0 |
| USY | 0.00 | 16.0 | 0.0 |
| RE/USY | 0.00 | 0.0 | 18.0 |
| Quasi-crystalline alumina | 27.0 | 20.0 | 20.0 |
| Micro-crystalline alumina | 13.00 | 13.0 | 13.0 |
| Low sodium colloidal silica | 1.50 | 5.0 | 5.0 |
| Acidic colloidal silica | 0.00 | 15.0 | 15.0 |
| RE component | 0.00 | 2.0 | 0.0 |
| Clay | 35.50 | 18.0 | 18.0 |

| Catalyst Description | Base Catalyst#3 | New catalyst#5 | New catalyst#6 |
|---|---|---|---|
| ABD | 0.77 | 0.74 | 0.75 |
| Attrition | 2.22 | 1.17 | 1.52 |
| Accessibility | 10.0 | 12.8 | 13.2 |
| Sample PV | 0.39 | 0.37 | 0.42 |
| SA BET | 251 | 291 | 286 |
| MSA | 133 | 143 | 146 |
| MIPV | 0.0550 | 0.0688 | 0.0651 |

| Catalyst Description | Base catalyst #1 | New Catalyst #1 | New Catalyst #2 | Base catalyst #2 | New Catalyst #3 | New Catalyst #4 |
|---|---|---|---|---|---|---|
| 430° F. + Conversion, wt % | 79.13 | 81.25 | 80.90 | 80.00 | 81.19 | 81.34 |
| Catalyst-to-Oil, wt/wt | 5.00 | 5.00 | 5.00 | 5.00 | 5.00 | 5.00 |
| Catalyst Selectivity @ 79% conversion | | | | | | |
| Coke | 8.17 | 7.11 | 7.01 | 8.37 | 7.17 | 7.44 |
| % coke reduction | | 13% | 14% | | 14% | 11% |
| 650° F. + | 7.13 | 6.84 | 6.89 | 6.84 | 6.77 | 6.73 |
| % bottoms upgrading | | 4% | 3% | | 1% | 2% |

Again, the deactivated catalysts showed enhanced mesoporosity in the range of 6 to 40 nm compared to base catalysts as shown in the figure below. As seen before, the pore diameter distribution having a peak at a pore diameter of about 2 to 6 nm has around 23% of total pore volume and the pore volume of pores with diameter 6 to 40 nm is around 69% of total pore volume for the catalysts of the present invention. In the base catalyst, the pore volume contribution of pores with diameter around 2 to 6 nm is around 38% and that of pores with diameter 6 to 40 nm is 48%, indicating that the catalysts of the present invention showed enhanced mesopores in the range of 6 to 40 nm, which resulted in improved coke selectivity and bottoms upgrading as shown in the ACE testing results in the table below.

| Catalyst Description | Base Catalyst#3 | New catalyst#5 | New catalyst#6 |
|---|---|---|---|
| 430° F. + Conversion, wt % | 68.03 | 67.48 | 69.09 |
| Catalyst-to-Oil, wt/wt | 5.00 | 5.00 | 5.00 |

| Catalyst Description | Base Catalyst#3 | New catalyst#5 | New catalyst#6 |
|---|---|---|---|
| | Selectivity @ 68% conversion | | |
| Coke | 10.39 | 9.61 | 9.11 |
| % Coke reduction | | 8% | 12% |
| 650° F.+ | 11.80 | 11.49 | 11.45 |
| % bottoms upgrading | | 3% | 3% |

Example 5: In the example given below, where the catalysts of the present invention were prepared by the methods described above. It is clear from the table below that the catalysts of the present invention showed better binding and accessibility than the base case catalyst.

| Catalyst Description | Base catalyst #4 | New catalyst #7 | New catalyst #8 | New catalyst #9 | New catalyst #10 | New catalyst #11 |
|---|---|---|---|---|---|---|
| RE-Y zeolite | 21.0 | 0.0 | 0.0 | 0.0 | 0.0 | 0.0 |
| USY-1 | 0.0 | 25.0 | 0.0 | 0.0 | 0.0 | 0.0 |
| USY-2 | 0.0 | 0.0 | 0.0 | 25.0 | 0.0 | 25.0 |
| RE-USY | 0.0 | 0.0 | 26.0 | 0.0 | 26.0 | 0.0 |
| Small-pore zeolite | 6.0 | 6.0 | 6.0 | 6.0 | 6.0 | 6.0 |
| Quasi-crystalline alumina | 30.0 | 20.0 | 20.0 | 20.0 | 20.0 | 20.0 |
| Micro-crystalline alumina | 15.0 | 15.0 | 15.0 | 15.0 | 15.0 | 15.0 |
| Low sodium colloidal silica | 1.5 | 5.0 | 5.0 | 5.0 | 5.0 | 5.0 |
| Acidic colloidal silica | 0.0 | 15.0 | 15.0 | 15.0 | 5.0 | 5.0 |
| RE component | 0.0 | 1.0 | 0.0 | 1.0 | 1.0 | 1.0 |
| Clay | 26.5 | 13.0 | 13.0 | 13.0 | 23.0 | 23.0 |

| Catalyst Description | Base catalyst #4 | New catalyst #7 | New catalyst #8 | New catalyst #9 | New catalyst #10 | New catalyst #11 |
|---|---|---|---|---|---|---|
| ABD | 0.74 | 0.71 | 0.73 | 0.69 | 0.71 | 0.68 |
| Million | 2.07 | 1.45 | 1.07 | 1.40 | 1.48 | 1.99 |
| Accessibility | 10.0 | 13.2 | 13.2 | 13.8 | 10.9 | 14.7 |
| Sample PV | 0.46 | 0.42 | 0.40 | 0.39 | 0.43 | 0.41 |
| SA BET | 275 | 310 | 318 | 306 | 304 | 296 |
| MSA | 150 | 150 | 159 | 144 | 143 | 138 |
| MIPV | 0.0582 | 0.0740 | 0.0739 | 0.0757 | 0.0749 | 0.0738 |

Also, after the deactivation in presence of Ni, V and steam, the mesopores in the range of 5-20 nm were created which is absent in the base case catalyst. Again the pore diameter distribution having a peak at a pore diameter of about 2 to 6 nm has around 30% of total pore volume and the pore volume of pores with diameter 6 to 40 nm is around 60% of total pore volume for catalysts of the present invention, whereas the base case catalyst almost equal pore volume contribution from the above mentioned pore diameter ranges. Catalysts with 50% reduced colloidal silica also showed comparable pore volume contribution. The benefits of mesopores created in catalysts of the present invention are revealed in the ACE performance test with resid feed as shown in the table below.

| Catalyst Description | Base catalyst #4 | New catalyst #7 | New catalyst #8 | New catalyst #9 | New catalyst #10 | New catalyst #11 |
|---|---|---|---|---|---|---|
| 430° F. + Conversion, wt % | 74.47 | 76.99 | 76.82 | 76.99 | 77.01 | 76.35 |
| Catalyst-to-Oil, wt/wt | 5.00 | 5.00 | 5.00 | 5.00 | 5.00 | 5.00 |

-continued

| Catalyst Description | Base catalyst #4 | New catalyst #7 | New catalyst #8 | New catalyst #9 | New catalyst #10 | New catalyst #11 |
|---|---|---|---|---|---|---|
| | Selectivity @ 75% conversion | | | | | |
| Coke | 7.68 | 6.53 | 6.45 | 6.55 | 6.75 | 6.71 |
| % Coke reduction | | 15% | 16% | 15% | 12% | 13% |
| 650° F. + | 8.77 | 8.94 | 9.09 | 8.95 | 8.93 | 8.91 |

The invention claimed is:

1. An FCC catalyst composition comprising a first zeolite of about 2 to about 50 wt % selected from the group of one or more ultra stabilized or rare earth exchanged ultra stabilized Y with a SiO2/Al2O3 ratio greater than 6.5, optionally a second zeolite of 0 to about 50 wt % of one or more rare-earth exchanged Y zeolite, optionally 0 to 30 wt % of small to medium pore zeolite, about 5 to about 45 wt % alumina from a quasicrystalline boehmite source, about 0 to about 35 wt % alumina from a microcrystalline boehmite source, a first silica source of about 0 to about 20 wt %, a second silica source of about 2 to about 30 wt %, about 0.1 to about 10 wt % one or more rare earth components as oxide and the balance clay, wherein the FCC catalyst has about 20 to about 30% of the total pore volume contributed by pores at a diameter of about 2.0 to about 6 nm and about 55 to about 70% of the pore volume of pores at a diameter of about 6 to 40 nm.

2. The FCC Catalyst of claim 1 wherein the first zeolite is one or more ultra stabilized Y zeolites.

3. The FCC Catalyst of claim 1 wherein the first zeolite is one or more rare earth exchanged ultra stabilized Y zeolites.

4. The FCC Catalyst of claim 1 wherein the one or more rare earth components comprise lanthanum, yttrium, cerium or mixtures thereof.

5. The FCC Catalyst of claim 1 wherein the one or more rare earth components comprise lanthanum.

6. The FCC Catalyst of claim 1 wherein the one or more rare earth components are added to the catalyst as hydroxide, chloride, oxide, nitrate, sulfate, oxychlorides, acetates, or carbonates.

7. The FCC Catalyst of claim 6 wherein the one or more rare earth components comprise lanthanum nitrate.

8. The FCC Catalyst of claim 1 wherein the medium pore zeolite comprises ZSM-5, ZSM-11, ZSM-22, Ferrierite, or mixtures thereof in the amount of greater than 0 to 30 wt %.

9. The FCC Catalyst of claim 1 wherein the first silica source comprises sodium stabilized colloidal silica in the amount of greater than about 0 to about 20 wt %.

10. The FCC Catalyst of claim 1 wherein the second silica source comprises acidic colloidal silica or ammonia stabilized colloidal silica or low-sodium stabilized colloidal silica or polysilicic acid, or mixtures thereof.

* * * * *